United States Patent [19]

Johnson et al.

[11] Patent Number: 5,437,660
[45] Date of Patent: Aug. 1, 1995

[54] TISSUE ABLATION AND A LATERAL-LASING FIBER OPTIC DEVICE THEREFOR

[75] Inventors: Douglas E. Johnson, Houston, Tex.;
Hany M. G. Hussein, Costa Mesa;
Marvin P. Loeb, Huntington Beach,
both of Calif.

[73] Assignee: Trimedyne, Inc., Irvine, Calif.

[21] Appl. No.: 814,708

[22] Filed: Dec. 30, 1991

[51] Int. Cl.⁶ ............................................. A61B 17/22
[52] U.S. Cl. ...................................... 606/15; 606/17;
606/7; 606/16
[58] Field of Search .................... 606/2, 3, 7, 10–17;
128/395–398, 4, 6

[56] References Cited

U.S. PATENT DOCUMENTS

| | | | |
|---|---|---|---|
| 4,445,892 | 5/1984 | Hussein et al. | 606/7 X |
| 4,519,390 | 5/1985 | Horne | 606/15 |
| 4,699,463 | 10/1987 | D'Amelio et al. | 128/4 X |
| 4,785,815 | 11/1988 | Cohen | 606/7 X |
| 4,819,632 | 4/1989 | Davies | 606/7 |
| 4,830,460 | 5/1989 | Goldenberg | 606/17 X |
| 4,832,024 | 5/1989 | Boussignac et al. | 606/7 |
| 4,848,339 | 7/1989 | Rink et al. | 606/15 X |
| 4,950,266 | 8/1990 | Sinofsky | 606/15 X |
| 5,020,995 | 6/1991 | Levy | 606/15 X |
| 5,041,121 | 8/1991 | Wondrazek et al. | 606/15 X |

OTHER PUBLICATIONS

McPhee, *Lasers in Urologic Surgery*, 2d ed., Year Book Medical Publishers, Inc., Chicago, Ill. (1989), pp. 41–49.
McPhee, *Lasers in Urologic Surgery*, Year Book Medical Publishers, Inc., Chicago, Ill. (1985), pp. 94–102.
Beisland and Sander, Urol. Res. 12:257–259 (1984).

*Primary Examiner*—Peter A. Aschenbrenner
*Attorney, Agent, or Firm*—Olson & Hierl, Ltd.

[57] ABSTRACT

A method for removing unwanted material in a body lumen, cavity or organ provides the steps of using an endoscope or other viewing system to position a suitably sized lateral-lasing fiber optic device axially at one or more places in a body lumen, cavity or organ and delivering a predetermined amount of light energy for a predetermined period of time laterally in one or more directions, while delivering a biocompatible fluid at a predetermined rate of flow. The distal end of the lateral-lasing fiber optic device includes a reflectively-coated metal tip, which is capable of directing, by reflection, the light energy from the optical fiber laterally from the longitudinal axis of the light energy carrying optical fiber and outwardly toward a target tissue region.

29 Claims, 5 Drawing Sheets

TISSUE ABLATION AND A LATERAL-LASING FIBER OPTIC DEVICE THEREFOR

FIELD OF THE INVENTION

The present invention relates to medical procedures and devices for ablating or coagulating tissue to effect the removal of unwanted material from body lumens, including blood vessels or ducts, cavities or organs, and more particularly to (a) transurethral laser resection of the prostate to remove unwanted tissue and increase urine flow, (b) coagulation or ablation of the endometrial lining of the uterus to stop excessive bleeding, (c) coagulation of bleeding blood vessels and (d) coagulation or ablation of tumors.

BACKGROUND OF THE INVENTION

Treatment of benign prostatic hyperplasia is one of this nation's major health-care expenses, as evidenced by the fact that transurethral resection of the prostate is second only to cataract extraction as the major operation most costly to Medicare. For the approximately 450,000 prostatectomies performed annually in the United States, hospitalization expenses and physician charges (not including costs for nonoperative evaluation and treatment) approach five billion dollars. The surgical procedure constitutes over a third of the major operations performed by urologists, and the operative and the clinical activities associated with it involve nearly a quarter of the urologist's time. Mortality for the procedure has been reduced to 0.2% over the last 27 years, but the incidence of immediate postoperative morbidity:has remained unchanged at 18%. The high cost of the procedure, not only in physician time but also in medical expense and patient morbidity, has therefore caused urologists to seek cheaper and less morbid ways of treating patients with benign prostatic hyperplasia.

During the last decade, as a result, a variety of alternative treatment methods have been introduced, including watchful waiting, medical management using alpha blockers or androgen suppression, insertion of prostatic stents and coils, balloon dilation, prostatic hyperthermia, and transurethral incision. None of these methods has proved superior to transurethral resection, and the majority of patients with bladder-outlet obstruction continue to require hospitalization for this procedure to relieve their symptoms.

The procedure of transurethral resection includes the step of electrically heating an insulated loop of wire in a electrocautery device and slowly drawing the heated loop back and forth longitudinally within the prostate to cut and cauterize tissue, creating a series of furrows along the length of the prostate until the lumen has been treated circumferentially. This procedure typically takes 45-60 minutes of physician's time to perform and considerable skill. If areas are missed or inadequately treated, an unsatisfactory treatment may result. Glycine, sorbitol-mannitol solution or sterile water, which are not as physiologically biocompatible as saline, are used as a cooling fluid, because saline will short-circuit the electrical power used to heat the loop and can cause harm to the patient.

Transurethral resection typically results in three to six days of bed stay at considerable cost, one to two weeks of recuperation time, substantial post-operative pain and bleeding, and approximately 10% of the patients require a blood transfusion. Up to 5% of the men who undergo this procedure suffer incontinence, and impotence results in up to 15%.

Although transurethral laser prostatectomy has held great theoretical interest, it has heretofore been impractical because of the difficulties in simply, accurately and effectively directing light energy into the tissue of the prostate. Urologists have attempted to apply laser photo irradiation for treatment of prostatic disease. McPhee, in *Lasers in Urologic Surgery*, 2d ed., Year Book Medical Publishers, Inc., Chicago, IL (1989), pp. 41-49 and in *Lasers in Urologic Surgery*, Year Book Medical Publishers, Inc., Chicago, IL (1985), pp. 94-102 describes employing light energy from a neodymium:YAG laser following transurethral prostatectomy in order to improve hemostasis and reports satisfactory postoperative voiding patterns. However, his technique was relatively cumbersome. Moreover, McPhee reports that he encountered some difficulty controlling bleeding of larger vessels at the vesical neck. Beisland and Sander, Urol. Res. 12:257-259 (1984) describe using light energy from a neodymium:YAG laser via a flexible laser cable three to four weeks after conventional transurethral prostatectomy in order to treat localized prostatic cancer, but report that it was found necessary to insert the flexible laser cable into the prostatic cavity through a suprapubic trocar cystoscope. While the procedure was well tolerated and void of serious complications, and while the preliminary results were encouraging, a surgical incision, albeit small, is still necessary, with the attendant risk of infection and extended hospital bed stay.

U.S. Pat. No. 4,445,892 to Hany M. Hussein, Marvin P. Loeb and Harvey S. Weiss teaches a dual balloon catheter device which is provided with two spaced and expandable balloons for occluding a segment of a blood vessel between the balloons. The dual balloon catheter device also includes a first channel for flushing the occluded segment, an optical system for use in the segment, a longitudinally movable and rotatable mirror or prism for directing light energy at an angle of 90° to the axis of the catheter, and a second channel for introducing fluid into the blood vessel distally of the device. Such a device is likely to require the same 45-60 minutes of procedure time and a high level of operator skill.

U.S. Pat. No. 4,672,963 to Israel Barken teaches a surgical system for destroying unwanted internal structures which includes a laser device, an ultrasonic probe and a computer system. The ultrasonic probe provides data signals that are processed by the computer system to provide an image of the structures involved in the laser irradiation procedure. The laser device can be inserted in the body and, while moving through the obstructed lumen, is activated by the computer system to provide radiation capable of destroying internal tissue. By calibrating the effects of the laser device as a function of power, the surgical procedure can be controlled by including overlaying images of the regions already affected by the surgical procedures on the images previously provided by the ultrasonic probe. This image reconstruction can be performed in real time providing immediate feedback to the attending physician. The computer system can also monitor system parameters such as laser power. This system has particular application to procedures involving the prostate gland where the laser device can be inserted intraurethrally and the ultrasonic probe can be inserted intraurethrally or transrectally. However, this technique requires expensive equipment and, like conventional transurethral resection of the prostate, takes considerable time and skill.

U.S. Pat. No. 4,955,882 to Said I. Hakky teaches a resectoscope for prostate surgery which includes a rotating cutting element mounted within an outer sheath adapted to be inserted into the urethra. The cutting element has helical threads along the length thereof and a cutting blade at its distal end. The outer sheath has a covered distal end portion which extends beyond and over the cutting blade and has an opening therethrough adjacent the cutting blade. Within the outer sheath is an inner sheath surrounding the cutting element except for the cutting blade. An optical fiber which is optically coupled to a laser is positioned within the space between the inner and outer sheaths and extends along the length of the inner sheath to a position adjacent the cutting blade. The optical fiber is surrounded by a third sheath and is adapted to be moved by the rotation of the cutting element so that the beam of light energy from the optical fiber advances through tissue to cut and coagulate the resected area before the cutting blade of the cutting element reaches the resected tissue. Irrigation fluid is provided to the area between the inner and outer sheaths and is withdrawn through the inner sheath. A telescope is also provided through the cutting element of reviewing the area being resected. The lack of accuracy of such a cutting device, with the risk of damage to the bladder sphincter, perforation of the prostate and damage to the rectum and intestines, makes this device less desirable than conventional electrocautery resection.

U.S. Pat. No. 4,449,528 to David C. Auth, Dale M. Lawrence and Tim R. Majoch teaches a miniaturized, endoscopically deliverable thermal cautery probe for cauterizing internal vessels. The probe is applied to tissues cold. Thereafter, a relatively large number of electric heating pulses of equal energy is then applied to an internal heating element in the probe. The probe has an internal heating element in direct thermal contact with an active heat-transfer portion that has a low heat capacity to insure quick heating and subsequent cooling, thereby adequately coagulating tissue while minimizing heat penetration and resulting tissue damage. The electrical power applied to the probe is continuously measured and is terminated when the energy delivered reaches a preset value. The number of such pulses applied to the probe, hence the total energy delivered, may be present while the duration of the period during which the pulses were applied is displayed. Alternatively, the duration of the period during which such pulses applied, hence the total energy delivered, is displayed. The heating element for the probe is a controlled breakdown diode which as a breakdown voltage that is a function of its temperature so that the temperature can be controlled. Again, glycine is used as a cooling fluid, since saline cannot be used in the presence of an electrical device. The heating element has a resistance of greater than 0.5 ohm to provide adequate power dissipation with relatively low currents. A washing fluid, preferably flowing along the outside of the probe toward its tip, cleans blood from the tissue to be coagulated to make the source of blood more readily visible. The risk of excessive heat penetration from such a device to the rectum and intestine makes this device less desirable than conventional electrocautery resection.

U.S. Pat. No. 4,672,961 to David H. Davies teaches an apparatus and method for retrolasing plaque deposits in a coronary artery to remove the same, which includes a tip assembly on the end of a flexible inner tube containing optical fibers that are slidable along a guide wire. The top assembly includes a reflective surface rearwardly of a front face that directs light energy supplied through the optical fibers in a rearward direction through a window portion to a focal point externally of the tip assembly. The deposit is removed as the top assembly is moved in a rearward progression back through the deposit. Such a device entails the same to and from, longitudinal movement and periodic rotation as electrocautery resection to produce a circumferential result, requires a similar 45-60 minute procedure time and entails significant operator skill, without predictable results.

U.S. Pat. No. 4,646,737 to Hany M. Hussein and Marvin P. Loeb teaches a heat applying medical device for applying localized heat to a portion of a patient's body. Generally, the heat applying medical device includes a lights transmitting conduit and a heat generating element which converts transmitted light into heat. A suitable exterior tube can also be provided for guidance, strength and delivery of fluids. The heat applying medical device can be used to cauterize or destroy tissue, or alter or remove deposits from lumens. The heat applying medical device can also serve as part of a system which provides the light and measures the temperature of the element. While this device produces localized heating and ablation of tissue, the risk of heat penetration into adjoining tissues and organs makes it less desirable than conventional electrocautery resection.

Endometrial ablation of the uterus in females, using an electrocautery, like in resection of the prostate, involves slowly moving an electrically heated wire loop along the inner wall of the uterus under direct vision, cutting and coagulating tissue in furrows, until the entire inner surface of the uterus has been treated. The procedure generally takes 45-60 minutes of physician time and considerable skill. In addition to significant pain and bleeding, substantial fluid flow is required to distend the uterus, which can cause excess absorption of fluid by tissues and leakage into the abdominal cavity, with risk of infection. If an area is missed or inadequately treated, an unsatisfactory treatment may result, and inadvertent perforation of the uterus could be extremely dangerous to the patient.

U.S. Pat. No. 4,834,091 to Douglas E. Ott teaches a surgical technique which uses a neodymium:YAG laser to treat the uterus while the uterus is kept distended by the flow of saline into the uterine cavity. The surgical technique includes the hysteroscopic insertion of a retrievable ostial plug into the tubal ostia of each fallopian tube so that the saline does not flow through the fallopian tubes during the period of time in which the laser is used to treat the uterus. At the conclusion of the laser treatment, the retrievable ostial plugs are hysteroscopically retrieved and withdrawn. Such a system entails an even longer period of time and special skills in the placement of the ostial plugs, with little improvement in procedure safety.

U.S. Pat. No. 4,836,189 to Jimmie B. Allred, III, Richard A. Kokosa, Allan I. Krauter and Richard W. Newman teaches a video hysteroscope which has an elongated flexible insertion tube containing a video imaging head at its distal end, with a channel for a surgical laser fiber and a saline channel which emits a continuous stream of saline solution distally from the head. The articulation section is kept as short as possible, and is limited to a maximum deflection of about 30 degrees. This system again requires significant operator skill and 45-60 minute of procedure time, and the limited 30° angle of deflection does not permit some portions of the uterus to be treated, resulting in an incomplete procedure and potential regrowth of the endometrium.

SUMMARY OF THE INVENTION

The present invention provides a relatively simple, low-risk, virtually bloodless, painless and rapid method for ablation and coagulation of tissue to effect the removal of unwanted material in a body lumen, cavity or organ using a lateral-lasing fiber-optic device under endoscopic or other viewing. Another advantage of the present invention is that it provides a lateral-lasing fiber-optic device using light energy from a laser, instead of electrical energy from an electrocautery device, to perform various medical procedures, such as transurethral laser resection of the prostate to remove unwanted tissue and increase urine flow and ablation of the endometrial lining of the uterus to stop excessive bleeding.

The method contemplated by the present invention utilizes an endoscope or like viewing device to position in a body lumen, cavity or organ a lateral-lasing fiber-optic device. This lasing device preferably has a reflectively coated metal tip at its distal end. The coated metal tip is capable of directing by reflection the light energy emitted from the optical fiber laterally from the axis of the optical fiber, and delivering a predetermined amount of light energy for a predetermined period of time in one or more directions, without substantial to- and-from longitudinal movement of the lateral-lasing fiber-optic device, while delivering bicompatible fluid at a predetermined rate of flow to control the temperature of the metal tip and the target tissue. The unwanted tissue is partially ablated and the remainder is coagulated to the desired depth. As a result, thermal necrosis and ultimate absorption or dissolution of the unwanted material is achieved.

Prior to laser irradiation the tissue to be irradiated may be infused with a photoactive agent.

DESCRIPTION OF THE PREFERRED EMBODIMENTS

Figure 1:
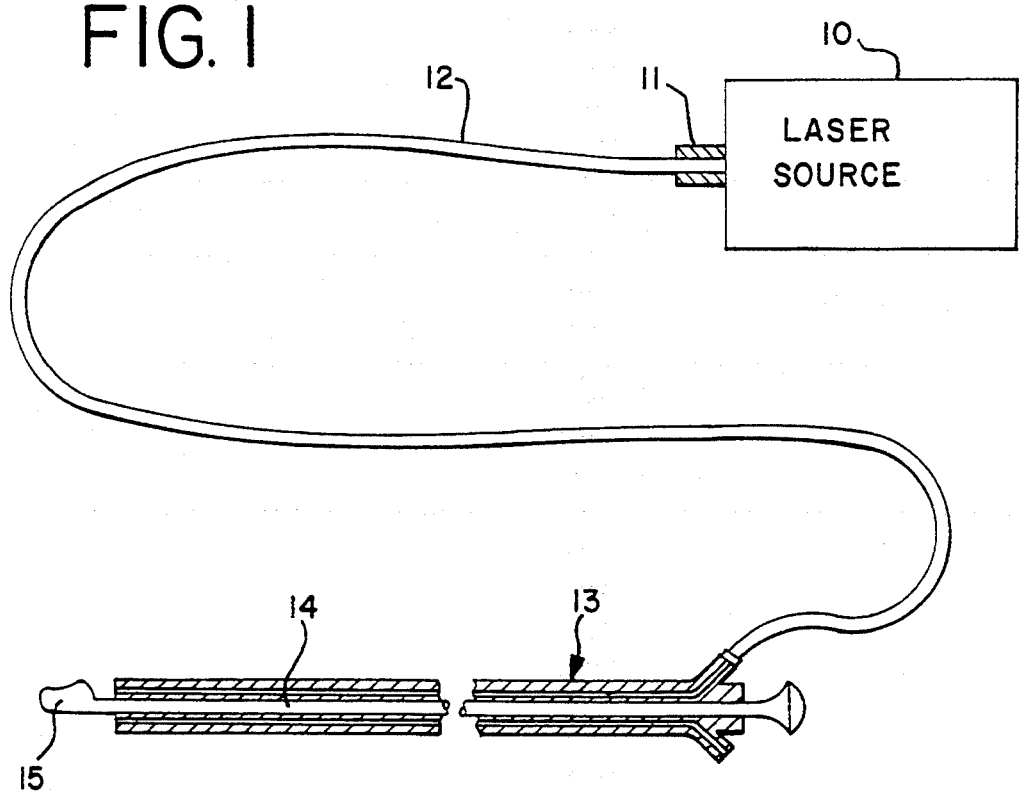
FIG. 1 is a fragmentary, schematic view of a laser and a lateral-lasing fiber-optic device, in which an optical fiber, optically and mechanically coupled to the laser, extends through an endoscope to a reflectively coated metal tip at the distal end of the optical fiber, and which has been constructed in accordance with the principles of the present invention.
Figure 2:
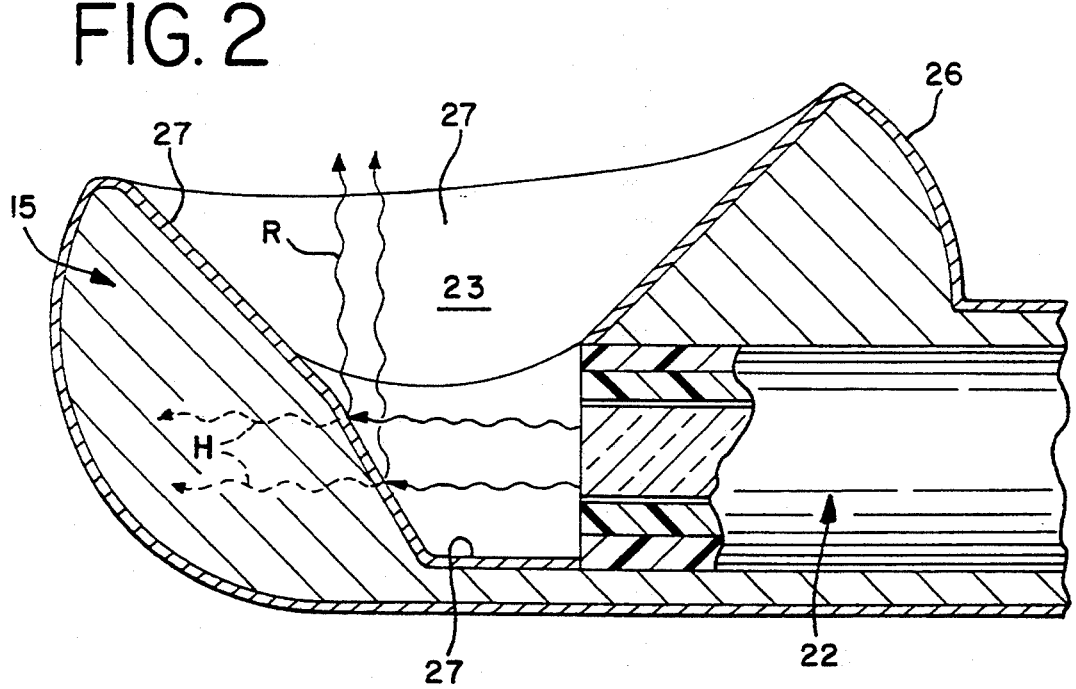
FIG. 2 is an expanded, fragmentary, cross-sectional view of the lateral-lasing fiber-optic device of FIG. 1.

Referring to FIG. 1, a laser source 10 is connected by a light energy coupling device 11, consisting of female and male components (not shown), to an optical fiber 12, which can extend through an endoscope 13. A lateral-lasing fiber-optic device 14, which preferably is provided at its distal end with a bulbous metal tip 15, is connected to optical fiber 12. The metal tip can have any convenient configuration, however. The metal tip 15 is coated with a reflective material. Metal tip 15 of lateral-lasing fiber-optic device 14 is shown in greater detail in FIG. 2. Optical fiber 22, at whose distal end is mounted metal tip 15, preferably coated in its entirety with reflective material 26, is connected at its proximal end to laser source 10. Reflective surface layer 27 within cavity 23 of tip 15 may be flat, a parabola or otherwise curved and is positioned so that the region of reflective surface 27 directly opposite optical fiber 22 is inclined at an angle, preferably of approximately 45° from the longitudinal axis of optical fiber 22. Reflective surface 27 receives laser light energy from optical fiber 22 and directs most of the received energy outwardly by reflection with divergence angles of approximately 45° to 135° laterally from the axis of optical fiber 22. Preferably, the center of the arc or cone of the outwardly directed energy is about 90° from the longitudinal axis of optical fiber 22. The outwardly directed energy is designated by R in the FIGURES, while energy consumed by incidental heating of the metal tip is designated by H. Temperature of the metal tip may be sensed and monitored by any convenient temperature sensing means known in the art. See, for example, U.S. Pat. No. 4,646,737 to Hussein and Loeb.

The method of ablating and coagulating tissue to achieve, usually through vaporization and thermal necrosis, the removal of unwanted tissue or material in a body lumen, cavity or organ, can be effected by using an endoscope 13 or other suitable viewing system to position in the desired place in a body lumen, cavity or organ a lateral-lasing fiber-optical device such as device 14 (FIG. 1) while delivering to the irradiated region throughout the lasing procedure saline, a glycine solution, a sorbitol-mannitol solution, sterile water or other biocompatible fluid at a predetermined rate to control the temperature of metal tip 15 as well as that of the target tissue. At the same time a predetermined amount of light energy is delivered from a laser source for a predetermined period of time in each of one or more directions, preferably in four equal or unequal sized quadrants, to achieve the desired zone of tissue coagulation. This irradiation is carried out usually without substantial longitudinal movement of metal tip 15 during the lasing, except as may be necessary to maintain proper placement of the lateral-lasing fiber-optic device opposite the target tissue.

The viewing system for properly placing the lateral-lasing fiber-optic device 14 in the prostate or uterus, or other body lumen, organ or cavity, may be an endoscope, rigid or flexible, such as a cystoscope with a diameter of about 21 to 25 French, preferably 23 French, or a hysteroscope, of conventional size. A magnetic resonance imaging system, an ultrasound imaging system, an X-ray or fluoroscopic imaging system or any other suitable viewing system may also have utilized in lieu of or in addition to the aforementioned viewing systems.

In a preferred embodiment, the entire outer surface of metal tip 15, instead of only reflective surface 27, is reflectively coated to minimize the amount of heat radiated by metal tip 15.

Preferably, tissue does not touch the light reflective surface 27 of metal tip 15 during lasing as the tissue may adhere, disrupt the reflection of laser energy and cause over-heating of metal tip 15 by excessive absorption of light energy.

Figure 3:
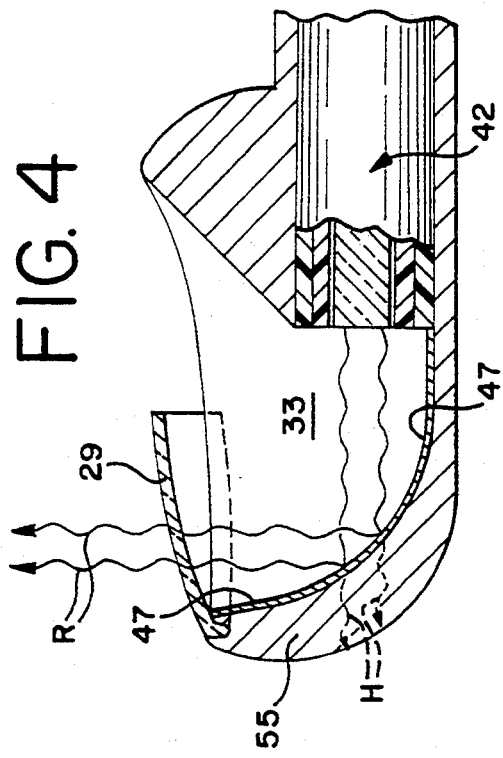
FIGS. 3, 4, 5 and 6 are cross-sectional views showing alternative embodiments of the lateral-lasing fiber-optic device of FIG. 1 in which the laser energy beam emitting cavity is protected by an operculum, i.e., a covering.

In an alternative embodiment shown in FIG. 3 an operculum in the form of one or more, i.e., a plurality of, metal ribs 28 is positioned over cavity 30 to prevent tissue from contacting reflective surface layer 37 of metal tip 25 mounted to optical fiber 32. Metal ribs 28 can be made of platinum or stainless steel, may be plated with gold, copper or silver for enhanced light reflectivity and can have a round, semicircular, square, triangular or other cross section. If desired, a heat insulating layer can be provided between reflective surface layer 37 and metal tip 25. Moreover, reflective surface layer 37 need not be integral with metal tip 25 but can be an inset as well.

Figure 4:
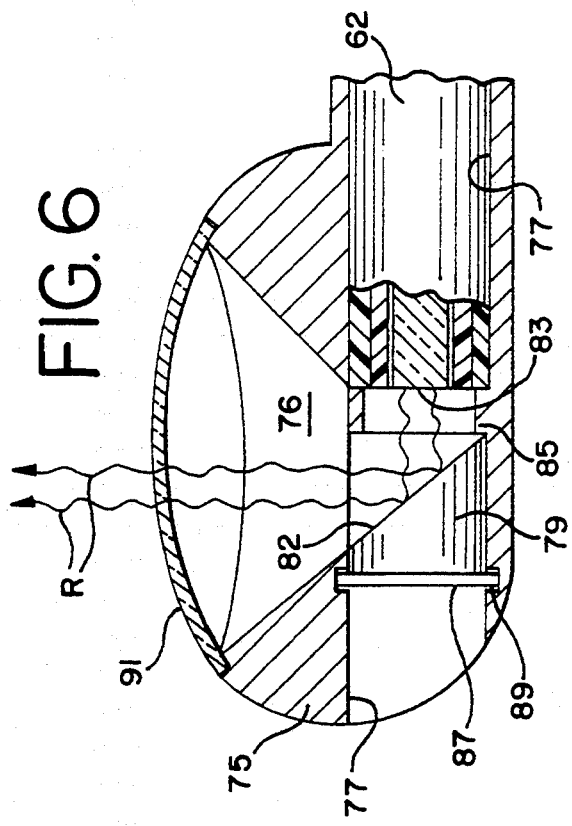

FIG. 4 shows, in another embodiment, a transparent baffle or canopy 29, made of a material transparent to the light energy being used, which partially covers cavity 33 in metal tip 55 mounted to optical fiber 42 to prevent tissue from contacting reflective surface 42. Canopy 29 an be made of quartz, fused silica, heat resistant or fused silica and glass sold under the tradename "Pyrex". Canopy 29 can also extend into cavity 33 and support an inset such as a mirror or a prism for directing light energy laterally outwardly from cavity 33.

Figure 5:
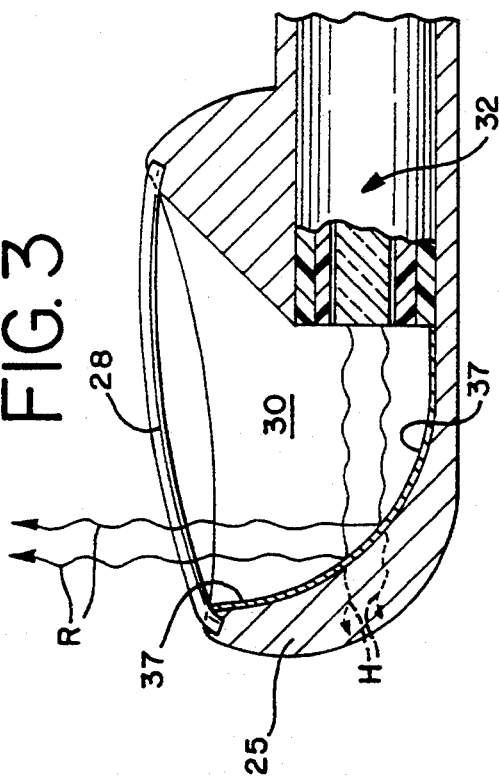

In yet another embodiment, shown in FIG. 5, canopy 31 is transparent and covers cavity 35 in tip 65 mounted to fiber optic 52 in its entirety, again to prevent tissue from contacting reflective surface layer 57. If desired, a fluid port or vent port can be provided in canopy 31 or tip 65.

Figure 6:
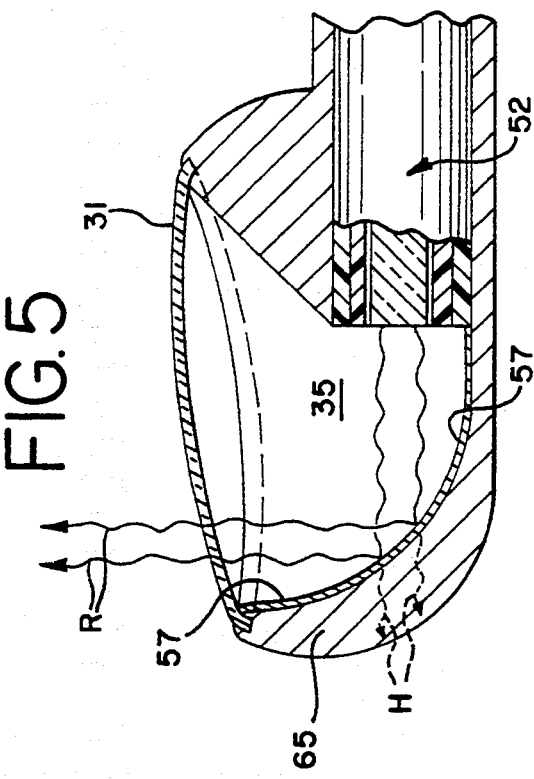

The presently contemplated tissue ablation device also can have a tip design as shown in FIG. 6 where tip 75 defines cavity 76 and a through passageway 77 with abutment 85 situated at an intermediate location within passageway 77. The proximal end of passageway 77 receives the distal end of optical fiber 62 while the distal end of passageway 77 receives mounted therein a cylindrical inset 79 having a reflective face 81 in juxtaposition to the distal end face 83 of optical fiber 62. Reflective face 81 is positioned relative to distal end face 83 so as to direct laterally outwardly through cavity 76 preferably substantially all of the laser energy beam that is conveyed to tip 75 via optical fiber 62 and emanates from end face 83.

Abutment 85 maintains a desired spacing between end face 83 of optical fiber 62 and reflective face 81 of inset 79. Locking ring 87 holds inset 79 in place within passageway 77. To this end, groove 89 that circumscribes the interior wall of passageway 77 is provided. Locking ring 87 nests in groove 89 when inset 79 is in place.

Canopy 91, again an operculum transparent to laser energy beam that exits laterally from cavity 76, covers the cavity in its entirely and protects against the accumulation of tissue debris or the like therewithin. Alternatively, in order to keep adjacent tissue out of cavity 76, one or more guard bars of the type illustrated in FIG. 3 can be provided across cavity 76.

The temperature of the metal tips such as 15, 25, 55, 65 and 75 can be controlled by a physiologically acceptable irrigation fluid that can be introduced through the endoscope, for example, and directed to flow past the metal tips while the laser source is energized.

The desired rate of fluid flow is about 20 to about 200 cubic centimeters per minute, preferably about 50 cubic centimeters per minute. Preferably, the irrigation fluid is warmed to body temperature. This rate of flow is preferably obtained by an irrigation pump or, alternatively, by utilizing a static pressure head, e.g., by hanging a bag of the irrigation fluid in an elevated position, usually approximately 2 to 4 feet above the cystoscopy table, preferably 2½ to 3 feet above the same, and adjusting a flow adjusting device to deliver the desired flow rate.

The light energy for irradiation is generated by a laser, preferably a neodymium:YAG laser, but may be chosen from any of a number of lasers, including a frequency-doubled neodymium:YAG laser, a KTP laser, an argon laser, a holmium:YAG laser or other light energy emitting laser, pulsed or continuous wave.

A rectal or trans-urethral ultrasound imaging system, a fluoroscope or other imaging device can be used to ascertain the shape, size and weight of the prostate and to estimate the desired contour of the tissue zone to be irradiated.

Figure 7:
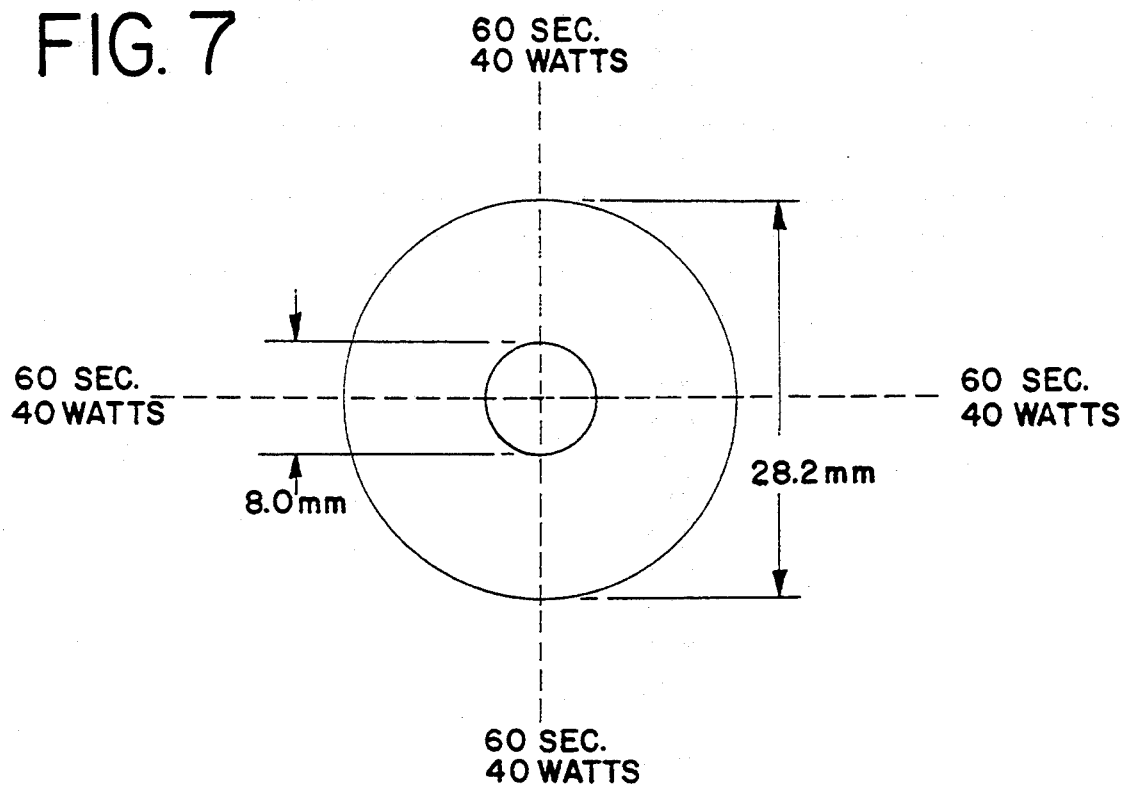
FIG. 7 is a schematic representation of the approximate, substantially circular damage zone contour in a potato model following the delivery of 40 watts of light energy from a neodymium:YAG laser through a lateral-lasing fiber-optic device for 60 seconds in each of the 12, 3, 6 and 9 o'clock positions.

Referring to FIG. 7, using an uncooked potato as a model because it exhibits similar light distribution (absorption) characteristics as the human prostate at a wavelength of approximately 1060 nanometers, and applying 40 watts of light energy from a neodymium:YAG laser through the lateral-lasing fiber-optic device 24 for 60 seconds at the 12, 3, 6 and 9 o'clock positions, or alternatively, at the 1:30, 4:30, 7:30 and 10:30 o'clock positions, during infusion of sterile water at 50 cc per minute, a consistent, generally spherical damage zone can be obtained in the potato. The diameter of the damage zone measured approximately 2.8 centimeters.

Since the human prostate is generally oval in cross section, usually it is preferable to produce an oval zone of tissue ablation and coagulation, thereby reducing the risk of damage to the prostatic capsule and surrounding veins at 12 o'clock and the prostatic capsule and underlying rectum at 6 o'clock.

In the case of an average-sized prostate of oval cross section and a weight of 25 to 35 grams, to achieve the desired oval zone of tissue coagulation, the preferred power level, duration of light energy emission and fluid flow rate are such as to elevate the tissue temperature in the desired zone of treatment to a valve of about 60° C. to about 100° C. To this end, approximately 40 watts for approximately 30 seconds in the 12 and 6 o'clock positions and approximately 60 seconds in the 3 and 9 o'clock positions, respectively, are applied. An aggregate of approximately 7,200 joules of energy, with an irrigation fluid flow rate of about 50 cc per minute throughout the procedure, is usually applied under such conditions. The total amount of energy applied during the treatment of the prostate can be in the range of about 4,500 joules to about 10,000 joules.

Figure 8:
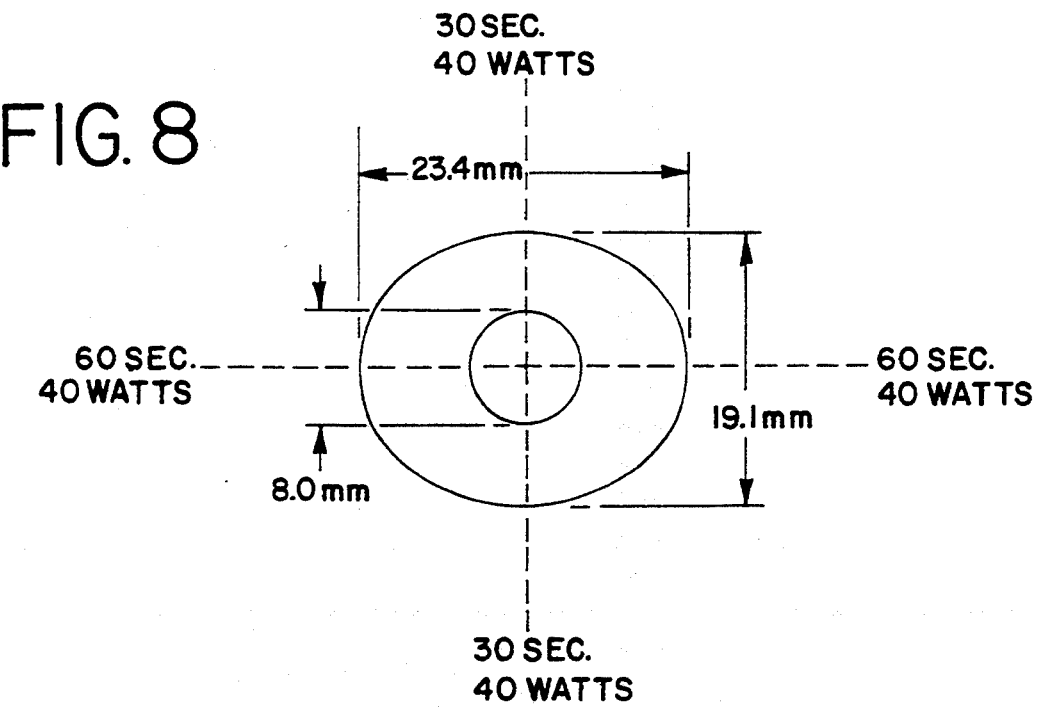
FIG. 8 is a schematic representation of the approximate, substantially oval damage zone contour in a potato model following the delivery of 40 watts of light energy from a neodymium:YAG laser through a lateral-lasing fiber-optic device for 30 seconds in the 12 and 6 o'clock positions and 60 seconds in the 3 and 9 o'clock positions.

To illustrate the effect of the above described technique, delivery from a neodymium:YAG laser to an uncooked potato model through a lateral-lasing fiber-optic device similar to that shown in FIG. 1 of 40 watts of light energy for 30 seconds in the 12 and 6 o'clock positions and 60 seconds in the 3 and 9 'clock positions, respectively, with an irrigation fluid flow rate of 50 cc per minute, produced an oval zone of coagulation of approximately 1.9 cm in height and 2.3 cm in width. The approximate contour of the damage zone is shown in FIG. 8.

Other methods for reducing the risk of damage to the prostatic capsule and adjoining tissues at the 12 and 6 o'clock positions are illustrated in FIGS. 9–12 and described below.

Figure 9:
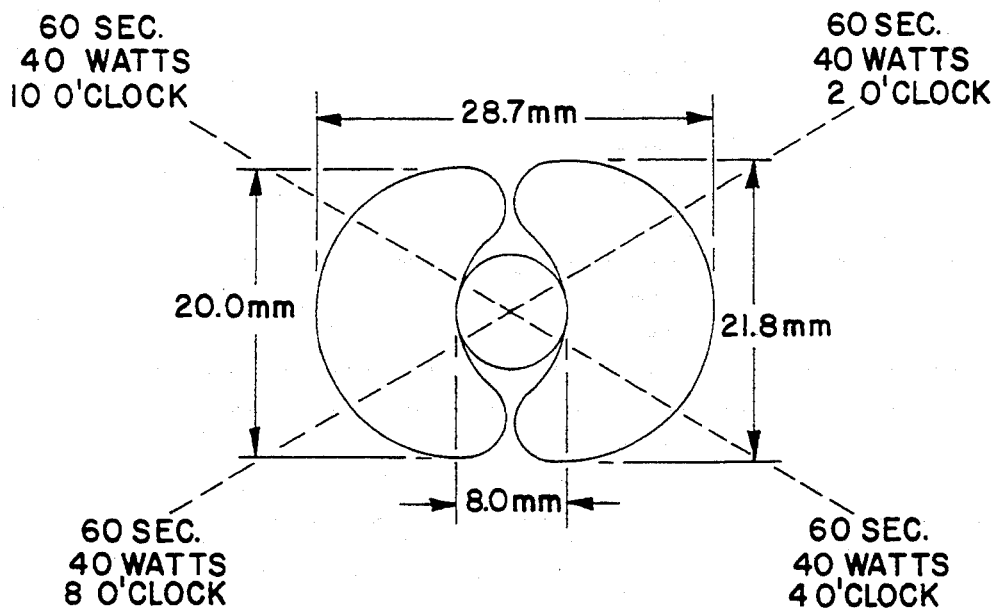
FIG. 9 is a schematic representation of the approximate, substantially oval damage zone contour in a potato model following the delivery of 40 watts of light energy from a neodymium:YAG laser through a lateral-lasing fiber-optic device for 60 seconds in each of the 2, 4, 8 and 10 o'clock positions.

Referring to FIG. 9, delivery of 40 watts of light energy from a neodymium:YAG laser through a lateral-lasing fiber-optic device to an uncooked potato for 60 seconds in each of four unequal sized quadrants at the 2, 4, 8 and 10 o'clock positions (a total of 9,600 joules), with fluid flow at 50 cc per minute, produces two kidney-shaped zones of damage of an overall size of approximately 2.0 to 2.2 cm in height and 2.9 cm in width.

Figure 10:
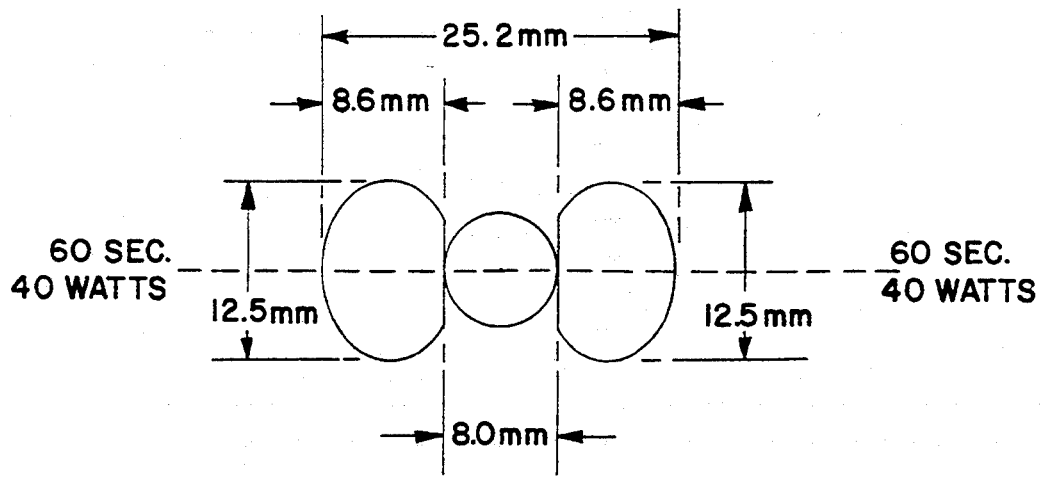
FIG. 10 is a schematic representation of the approximate damage zones in a potato model following the delivery of 40 watts of light energy from a neodymium:YAG laser through a lateral-lasing fiber-optic device for 60 seconds in each of the 3 and 9 o'clock positions.

Referring to FIG. 10, delivery of 40 watts of light energy from a neodymium:YAG laser through a fiber-optic lateral-lasing device to an uncooked potato for 60 seconds at each of the 3 and 9 o'clock positions, an aggregate of 4,800 joules of energy, with fluid flow at 50 cc per minute, produces two, approximately equal-sized, kidney-shaped zones of coagulation, each of approximately 1.25 cm in height and 0.86 cm in width.

Figure 11:
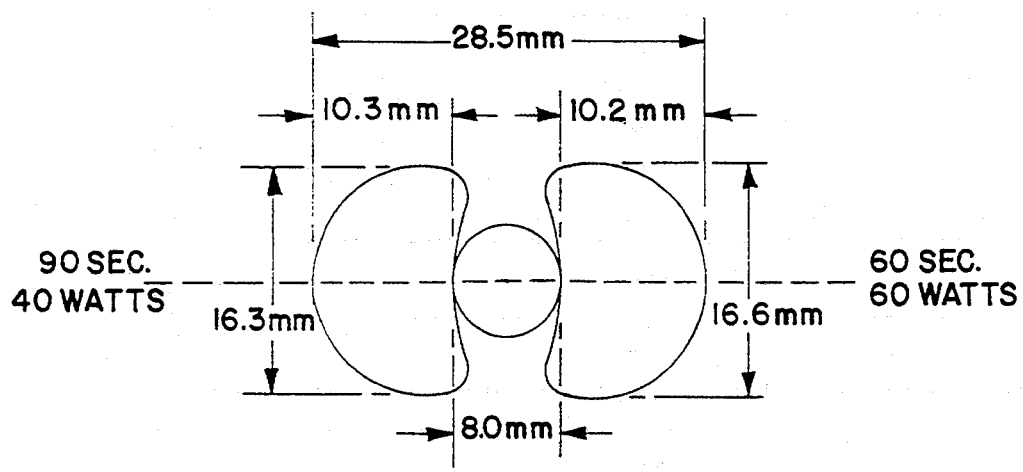
FIG. 11 is a schematic representation of the approximate damage zones in a potato model following the delivery of 60 watts of light energy for 60 seconds in the 3 o'clock position and 40 watts of light energy for 90 seconds in the 9 o'clock position.

As shown in FIG. 11, delivery from a neodymium:YAG laser through a lateral-lasing fiber-optic device to an uncooked potato of 40 watts of light energy for 90 seconds at the 3 o'clock position and 60 watts of light energy for 60 seconds at the 9 o'clock position, an aggregate of 3,600 joules of energy in each position (a total of 7,200 joules), with fluid flow at 50 cc per minute, produces two approximately equal-sized, kidney-shaped zones of damage, each of approximately 1.6 to 1.7 cm in height and 1.0 cm in width. These zones of damage are smaller than those shown in FIG. 9, due to the relatively lesser amount of energy delivered.

If a lower level of light energy is delivered for a proportionately longer period of time, even if a total of 7,200 joules of energy are delivered to the prostate, a relatively smaller zone of damage will result, due to heat dissipation from the treated tissue during the resulting longer period of irradiation.

Figure 12:
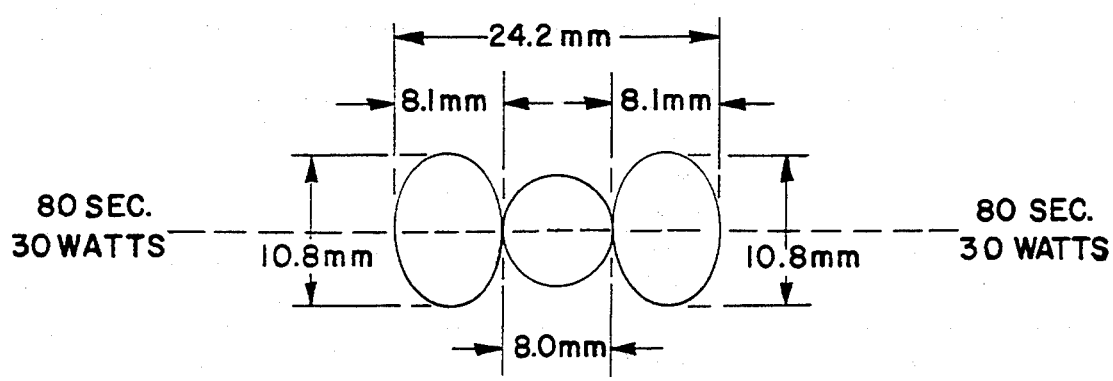
FIG. 12 is a schematic representation of the approximate damage zones in a potato model following the delivery from a neodymium:YAG laser through a lateral-lasing fiber-optic device of 30 watts of light energy for 80 seconds in the 3 and 9 o'clock positions.

As shown in FIG. 12, delivery from a neodymium:YAG laser through the lateral-lasing fiber-optic device 24 to an uncooked potato mold of 30 watts of light energy for 80 seconds at the 3 and 9 o'clock positions, an aggregate of 4,800 joules of energy, with fluid flow at 50 cc per minute, produces two approximately equal-sized, kidney shaped zones of damage, each of approximately 1.1. cm in height and 0.8 cm in width.

If the size of the prostate or length of the urethra requires, for example, in prostates substantially larger than 30 grams in weight, the cystoscope and the lateral-lasing fiber-optic device can be moved longitudinally approximately 2.25 centimeters and a second zone can be circumferentially or bilaterally lased in the same manner.

Alternatively, the lateral-lasing fiber-optic device can be moved relatively slowly through the lumen, or back and forth within the lumen, over a course appropriate for the length of the prostate or uterus, for a predetermined longer period of time in each of the four aforementioned quadrants. A longer time of irradiation is required, if this procedure is utilized, because the cumulative effect of tissue heating to the point of coagulation in a particular direction is diminished by movement of the lateral-lasing fiber-optic device. Also, if this technique is utilized, greater operator skill is required to keep the lateral-lasing fiber-optic device spaced at a substantially uniform distance from tissue or from contacting tissue and suffering damage therefrom as well.

In the case of a lateral-lasing fiber-optic device connected to a Nd:YAG laser by an optical fiber with a core diameter of 600 microns, at a distance of 20 mm in air, the diameter of the area of laser energy delivered to the tissue (spot size) is about 16.3 mm, due to a wider beam divergence from reflective surface 27 of metal tip 25, compared to a spot size of about 7.7 mm in the case of light energy emitted directly by an optical fiber at the same distance in air whose core diameter is likewise 600 microns. The potential for a greater area of light exposure and the emission of light energy lateral to the axis of the optical fiber, gives the lateral-lasing fiber-optic device an advantage over conventional optical fibers in applications such as those described herein.

The zone of damage will increase if the rate of fluid flow is decreased, and the damage zone will decrease if the rate of fluid flow is increased. At lower power levels, the damage zone is more severely affected by an increase or decrease in the rate of fluid flow.

The reflective coating material on the metal tip of the lasing device can be a metal such as gold, silver, copper, platinum or other reflective material. In one embodiment, the metal tip is made of a metal alloy, e.g. stainless steel.

In a further embodiment (FIG. 6), the metal tip can contain an inset reflector member, which can be a mirror, prism, or the like, in which case the amount of light reflected is relatively higher and the amount of light absorbed by the tip is relatively lower, resulting in reduced incidental heating of the metal tip. Alternatively, the inset member can be made of fused silica, sold under the trademark Pyrex, which has high thermal shock resistance, or diamond or sapphire. A reflective coating can be applied to the surface of such inset, if desired, by vacuum deposition of alternate layers of magnesium fluoride and cerium oxide films. The thickness and type of the reflective coating depends on the wavelength of the incident light energy and the angle of incidence thereto. Such coatings are known in the art.

In a laboratory experiment about 40 watts of neodymium:YAG laser energy was delivered to two lateral-lasing fiber-optic devices in air, one with a gold reflective coating only on the reflective surface within the cavity of the metal tip, and the other with a gold reflective coating over the entire outer surface of the metal tip. A thermocouple placed 1 cm from the side opposite the cavity of each device indicated a maximum temperature of 26.4° C. in the case of the metal tip 25 with a reflective coating only on the interior reflective surface 27, and 25.6° C. in the case of the metal tip whose entire outer surface was reflectively coated.

The optical fiber to which the metal tip is mounted may have a core diameter of about 200 to about 1000 microns, preferably about 600 microns. The proximal end of the optical fiber can incorporate an SMA-type or other optical fiber connector to a laser, which can provide light energy at various wavelengths from 300 nm to about 2,500 nm, from the ultraviolet to infrared, but preferably at a wavelength of 1064 nanometers, the wavelength generated by a neodymium:YAG laser. With special fiber optics, e.g., a zirconium fluoride fiber, wavelengths as long as 3,100 nm can be used.

Since the method described herein does not involve the use of an electric current, saline may be used for irrigating the treatment zone or region instead of a glycine solution, an amino acid containing solution. Alternatively, a sorbitol-mannitol solution or sterile water can be used for irrigation purposes. However, sterile water is hypotonic and, in excess, can be harmful to the patient.

McPhee, in the publications cited above, states that the uncooked potato has an extinction coefficient for light energy at a wavelength of approximately 1060 nanometers, similar to that of the R3327-AT prostatic cancer in F1 hybrid Copenhagen/Fisher rats, and tissue distribution comparable to that of the prostate in humans. In a series of experiments using uncooked potatoes as models, a central core having a diameter of approximately 0.8 centimeters was removed and, with continuous fluid flow at a rate of approximately 50 cubic centimeters per minute, varying amounts of light energy were applied at various positions for varying periods of time. Staining slices of the potato after lasing with iodine made the lesions produced by the light energy easy to demarcate and measure. The dimensions of the zones of damage produced are approximated in FIGS. 7 through 12. Reducing the power, even with an inversely proportionate increase in the duration of lasing, produced a smaller zone of damage, as illustrated in FIGS. 11 and 12.

While the density of the tissue from one potato to another will vary, the ratios of the sizes of the zones of damage illustrate the relative effects of delivery of laser light energy, as shown in FIGS. 7 through 12.

In another embodiment, to prevent destruction of the metal tip if the reflective coating thereof is burned away or the reflective surface is disrupted by (a) inadequate fluid flow for proper temperature control, (b) delivery of too high a level of light energy, (c) exposure to light energy for too long a period of time or (d) adherence of burned tissue if the reflective surface comes in contact tissue during laser use, the metal tip may contain a thermocouple, or other temperature sensing device, which is able to detect and transmit the temperature of metal tip to a logic circuit (not shown), which is programmed to (a) trigger an alarm, (b) reduce or increase the amount of light energy necessary to maintain the desired temperature, and/or (c) shut-down the laser if the temperature of metal tip exceeds or falls below pre-set temperature levels, which may vary from approximately 60° to 100° C.

Laser transurethral prostatectomy was satisfactorily performed in seven dogs. In each case, urinary continence was preserved. The technique proved to be a simple and safe procedure, and did not require catheter drainage.

Seven adult mongrel dogs weighing between 52 and 72 pounds were given general anesthesia, consisting of thiopental sodium in the amount of 3 to 4 milligrams per kilogram, and atropine in the amount of 1 milligram, followed by halothane sufficient to maintain anesthesia. Since the dogs' urethra is too small for insertion of a 23 French or larger cystoscope, a midline lower abdominal incision was used to expose the bladder, which was secured in place around a 0-chromic purse-string suture. The cystoscope was advanced into the prostatic urethra and, under direct vision, the lateral-lasing, fiber-optic device of the type shown in FIG. 1 was placed at the level of the verumontanum. Using a neodymium:YAG laser, varying amounts of power were applied during an appropriate rate of fluid flow for various periods of time at the 12, 3, 6 and 9 o'clock positions.

The first dog was sacrificed immediately and the prostate removed for histologic examination. The cystotomy in the remaining six dogs was closed using a 3-0 chromic catgut suture, the abdominal incision was closed with interrupted 2-0 vicryl sutures, and the skin was closed with fine wire in an interrupted fashion. No urinary catheter or drains were left indwelling at the end of the procedure. Each dog received 500 milligrams of chloramphenicol, an antibiotic, three times a day beginning on the day of surgery and for seven consecutive days thereafter. The dogs were allowed to drink and resume activity immediately after surgery. Over a period of weeks, the remaining tissue in the coagulation (thermal necrosis) zone was absorbed by the body or sloughed-off in a mucous-like effusion, with little or no particular matter appearing in the urine or mucous-like effusate.

The remaining dogs were sacrificed 8 weeks after surgery. At that time, the bladder, prostate and proximal urethra were removed, fixed in 10% neutral buffered formaldehyde solution (Formalin), and later sectioned and embedded in paraffin for histologic assessment. No animal was observed to have suffered bleeding, and only one required short-term urethral catheterization. Continence was maintained in all animals. Examination of the prostate immediately after lasing (Dog 1) acutely revealed a well-demarcated sphere of thermal necrosis having a diameter of approximately 2.6 centimeters. In the other six animals, the transurethral defects were proportional to the amount of light energy used. In each instance, after about eight weeks, transitional epithelium had relined the prostatic cavity, the adjacent parenchyma showed glandular atrophy and fibrosis, and the capsule of the prostate was intact.

In 20 human patients treated with laser transurethral prostatic resection, a 23 French or larger cystoscope was used, and the procedure was successfully carried out under endoscopic or other viewing in a manner consistent with the method described above.

A catheter was left in place in the urethra for a day or two to maintain urine flow, as some swelling of the prostate occurred from the thermal coagulation, which resolved without complication. In all cases, urine flow was slightly increased after removal of the catheter. The coagulated tissue was slowly absorbed by the body or sloughed-off in a mucous-like effusion with minimal particulate matter during a period of up to three to four weeks.

Urine flow increased daily during a period of two to three weeks after the procedure, from an average pre-procedure urine flow rate of about 9 cc per second to an average 14.75 cc per second approximately one month following the procedure.

There was little or no post-operative bleeding or pain, hospitalization was 1 to 2 days, no blood transfusions were required, the patients returned to normal activities after one to three days of recuperation at home, continence was preserved and erectile potency was unaffected.

Subsequently additional five human patients were treated with laser transurethral resection in the manner described above, except the input energy level, time of lasing and directions were 40 watts for 30 seconds at the 12 and 6 o'clock positions and 60 seconds at the 3 and 9 o'clock positions, respectively. The results were substantially the same as described above.

Some small popping sounds were occasionally heard and ruptures of the inner, treated surface of the urethra were occasionally observed with the input of 60 watts of Nd:YAG laser energy, possibly due to the creation of steam in pockets below the surface during lasing. Little or no bleeding and no adverse effects from these ruptures was seen, however. At lower light energy input levels, such as 40 watts of Nd:YAG laser energy, such popping sounds or ruptures were infrequently noted.

To treat excessive bleeding of the endometrial lining of the uterus, the lateral-lasing fiber-optic device may be inserted into the uterus through an endoscopic device and properly positioned in the center of and approximately 1 cm from the fundus of the uterus. Light energy from a neodymium:YAG laser may be delivered through the lateral-lasing fiber-optic device, with sufficient flow of a biocompatible fluid throughout the procedure to distend the uterus to an extent desirable to obtain visualization and keep tissue from contacting metal tip, at power levels of from 20 to 60 watts for 20 to 60 seconds, depending on the cross sectional dimensions of the distended uterus, which may be estimated by ultrasound imaging, at each of the 12, 3, 6 and 9 o'clock positions or 2,4, 8 and 10 o'clock positions, to obtain the desired depth of coagulation, approximately 4 to 7 mm.

Depending on the estimated length of the uterus, the lateral-lasing fiber-optic device may be withdrawn approximately 2.25 cm and the lasing procedure with fluid flow, both as described above, may be repeated. If appropriate, the above described lasing procedure with fluid flow may again be repeated in a third location.

As the cross-sectional size of the uterus decreases, the amount of energy and/or the amount of time may be reduced, and the rate of fluid flow may be adjusted to produce the desired distention of the uterus for proper visualization, while maintaining a lumen sufficient to prevent tissue from contacting the metal tip of the lateral lasing fiber optic device.

To minimize excessive fluid infusion into a body cavity or organ, the lateral-lasing fiber-optic device can be contained within a balloon in a manner similar to that shown in commonly-owned U.S. Pat. No. 4,470,407 to Hussein. The device-enveloping balloon can be made of a material which is transparent to the wavelength of light energy used, such as silicone film or polyurethane film of 0.05 mm to 1 mm in thickness, preferably about 0.2 mm to 0.5 mm in thickness, in the case of a Nd:YAG laser of 1064 nm. The balloon can be in a shape that is complementary to the interior contour of the organ, cavity of lumen being treated. For example, the balloon can be in a tubular, triangular shape for use in the uterus. Fluid is circulated in the balloon, which is distended to the interior surface of the body cavity, organ or lumen. Continuous fluid flow during lasing can optionally be utilized to maintain a desired temperature in the lasing region.

From the foregoing, it can be seen that a simple, safe, effective and rapid method of unwanted tissue removal from a body lumen, cavity or organ, using a lateral-lasing fiber-optic device, for example, to vaporize or coagulate prostatic tissue in the prostate or endometrial tissue in the uterus endoscopically, has been described.

Additionally, in the event a tumor or growth of tissue, an ulcer or one or more blood vessels in need of cauterization lie in a particular direction in a body lumen, cavity or organ, an endoscope or other viewing system can be used to properly position the lateral-lasing fiber-optic device to direct an appropriate amount of light energy from the laser for an appropriate period of time in the direction of the tumor or growth, ulcer or bleeding vessels to obtain the desired zone of ablation or coagulation. For example, the method described above may be used to ablate endometrial tissue in the abdominal cavity to treat endometriosis, to vaporize or coagulate cancerous tissue in the uterus, prostate or other body lumen, cavity or organ, or to cauterize an ulcer or bleeding blood vessel in the stomach or elsewhere.

Since tumors, due to generally inadequate circulation, are less able to dissipate heat, the lateral-lasing fiber-optic device may also be used to simply raise the temperature of a tumor by 5° to 6° centigrade for an appropriate period of time, generally 5 to 40 minutes, and selectively cause the death of the tumor cells, without creating sufficient heat to cause thermal necrosis of adjoining normal tissues.

Since the area of impinging light energy (spot size) emitted from lateral-lasing fiber-optic device is larger than that emitted from a conventional optical fiber, lateral-lasing fiber-optic device can be used to deliver light energy of an appropriate wave-length to activate a photo-active drug, such as a hematoporphyrin derivative, in which case an argon laser might be used, a psoralen, in which case an excimer or other ultraviolet light generating laser might be used, or the like, which photo-active drug has accumulated in the unwanted tissue as a result of the earlier administration of same to the patient.

In certain of the above instances, for example, in cauterizing a bleeding ulcer in the stomach, the presence of existing stomach fluids may reduce or negate the need for fluid flow. In other instances, for example, in removal of endometrial tissue in the abdominal cavity where little fluid exists, fluid flow or a spray of biocompatible liquid or a gas, such as carbon dioxide, may be used to control the temperature of metal tip and the target tissue.

The apparatus of this invention may be employed with conventional optical fibers, a suitable conventional laser, a logic system and coupling system therefor, the details of which, although not fully illustrated or described, will be apparent to those having skill in the art and an understanding of the necessary functions of such devices. The detailed descriptions of such devices are not necessary to an understanding of the invention and are not herein presented because such devices form no part of the present invention.

While this invention may be embodied in many different forms, this specification and the accompanying drawings disclose only some specified forms as examples of the invention. Accordingly it is intended that the foregoing disclosure and showing made in the drawings shall be considered only as an illustration of the principles of the present invention and not as a limitation.

We claim:

1. A method for the removal of unwanted tissue comprising the steps of:
   positioning an elongated lateral-lasing fiber optic device adjacent a selected region of the tissue to be removed;
   delivering to the selected region a biocompatible fluid at a predetermined rate of flow contiguous with the positioned lateral-lasing fiber optic device; and
   energizing the positioned lateral-lasing fiber optic device at a predetermined power level to emit continuous wave laser energy in a direction substantially transversely to the longitudinal axis of the lateral-lasing fiber optic device and so as to irradiate the selected region of the tissue to be removed for a predetermined time period to produce a zone of coagulation in the irradiated tissue.

2. The method according to claim 1, in which the biocompatible fluid is delivered at a flow rate in the range of 20 to 200 cubic centimeters per minute.

3. The method according to claim 1, in which said positioning is done by means of an endoscope.

4. The method according to claim 1, in which said positioning is adjacent to tissue in a body lumen, cavity or organ.

5. The method according to claim 1, in which said positioning is adjacent to the prostatic urethra.

6. The method according to claim 1, in which said positioning is adjacent to tissue in the uterus.

7. The method according to claim 1, in which said positioning is adjacent to the endometrium of the uterus.

8. A method for removing unwanted tissue in a body lumen, cavity or organ, which comprises the steps of:
   (a) using a viewing system to position in a body lumen, cavity or organ opposite said unwanted tissue a lateral-lasing fiber-optic device having at the distal end thereof a reflectively-coated metal tip mounted to an optical fiber, which tip is capable of directing by reflection the light energy from a laser laterally away from the axis of the optical fiber; and
   (b) delivering, while infusing a biocompatible fluid at a predetermined flow rate, or in the presence of sufficient fluid, a predetermined amount of light energy from a laser to said unwanted tissue for a predetermined period of time to obtain the desired zone of coagulation.

9. The method according to claim 8, in which the light energy is generated by a neodymium:YAG laser.

10. The method according to claim 8, in which the delivered light energy Is generated by a holmium laser.

11. The method according to claim 8, in which the light energy is delivered to the prostate.

12. The method in accordance with claim 1, wherein said unwanted tissue is infused with a photoactive agent prior to the delivery of light energy thereto.

13. The method in accordance with claim 1 wherein said light energy is delivered while the temperature of the tip is monitored.

14. A device for applying a laser energy beam to a selected body site comprising:
   an elongated, laser energy transmitting conduit having a proximal end and a distal end;
   a laser energy source optically coupled to the proximal end region of the conduit for transmitting laser energy along the conduit;
   a hollow, apertured bulbous element mounted on the distal end of said conduit and provided with an internal laser energy reflective surface so that a major portion of the laser energy transmitted by the conduit to the bulbous element impinges thereon and exits from the element laterally as a laser energy beam; said element defining a cavity within which the distal end of the conduit is received and further defining an aperture communicating with said cavity and positioned to one side of the laser energy path entering said cavity but in registry with the laterally exiting laser energy beam; and
   an covering over said cavity; said covering being permeable to the laser energy beam but preventing body tissue entry into said cavity, 15. A device for applying a laser energy beam to a selected body site comprising:
   an elongated, laser energy transmitting conduit having a proximal end and a distal end;
   a laser energy source optically coupled to the proximal end region of the conduit for transmitting laser energy along the conduit;
   a hollow apertured bulbous element mounted on the distal end of said conduit and provided with an internal laser energy reflective surface so that a major portion of the laser energy transmitted by the conduit to the bulbous element impinges thereon and exits from the element laterally as a laser energy beam; said element defining a cavity within which the distal end of the conduit is received and further defining an aperture communicating with said cavity and positioned to one side of the laser energy path entering said cavity but in registry with the laterally exiting laser beam; and
   a bar that extends longitudinally across said cavity and prevents body tissue entry into said cavity.

16. A device for applying a laser energy beam to a selected body site comprising:
   an elongated laser energy transmitting conduit having a proximal end and a distal end;
   a laser energy source optically coupled to the proximal end region of the conduit for transmitting laser energy along the conduit;
   a hollow, apertured bulbous element mounted on the distal end of said conduit and provided with an internal laser energy reflective surface so that a major portion of the Laser energy transmitted by the conduit to the bulbous element impinges thereon and exits from the element laterally as a laser energy beam, said element defining a cavity within which the distal end of the conduit is received and further defining an aperture communicating with said cavity and positioned to one side of the laser energy path entering said cavity but in registry with the laterally exiting laser energy beam; and a plurality of bars across said cavity that prevent body tissue entry into said cavity.

17. The device according to claim 14 wherein the covering is a laser energy transparent baffle that extends partially across said cavity, 18. The device according to claim 14 wherein the covering is a laser energy transparent lid over said cavity, 19. The device according to claim 14 wherein the covering is a laser energy transparent lid over said cavity and wherein the lid and said hollow apertured element together define a sealed space therebetween.

20. The device according to claim 14 wherein the laser energy beam exits the hollow element through said covering and in a direction substantially transverse to the major axis of the elongated laser energy transmitting conduit at the distal end region of the conduit.

21. The device according to claim 14 wherein an energy reflective surface layer for receiving and reflecting the laser energy transmitted by the conduit is provided within said cavity and in the path of the laser energy beam emitted from the conduit.

22. The device according to claim 14 wherein the energy reflective mirror surface is defined by a layer of gold.

23. The device according to claim 14 wherein a reflective coating is provided on the external surface of the hollow element.

24. The device according to claim 14 wherein the energy reflective surface is provided by an inset mounted in the hollow element and situated in the path of a laser beam exiting from said conduit.

25. The method in accordance with claim 1 wherein the lateral-lasing fiber optic device is energized to emit laser energy at a wavelength of about 1064 nanometers.

26. The method in accordance with claim 1 wherein the lateral-lasing fiber optic device is energized to emit laser energy at a wavelength generated by a holmium laser.

27. The method in accordance with claim wherein the lateral-lasing fiber optic device is energized to emit laser energy at a wavelength of about 1064 nanometers and at a power level of about 40 watts while said biocompatible fluid is delivered at a rate of about 50 cubic centimeters per minute.

28. The method in accordance with claim 27 wherein the lateral-lasing fiber optic device is positioned within prostatic urethra adjacent to a selected region of the prostate to be removed and said selected region of the prostate is irradiated for a time period of about 30 seconds.

29. The method in accordance with claim 27 wherein the lateral-lasing fiber optic device is positioned within prostatic urethra adjacent to a selected region of prostate to be removed and said selected region of the prostate is irradiated for a time period of about 60 seconds.

* * * * *

UNITED STATES PATENT AND TRADEMARK OFFICE
CERTIFICATE OF CORRECTION

PATENT NO. : 5,437,660
DATED : August 1, 1995
INVENTOR(S) : Douglas E. Johnson et al.

It is certified that error appears in the above-indentified patent and that said Letters Patent is hereby corrected as shown below:

Col. 1, line 33, after "morbidity" delete the colon (:).

Col. 4, line 22, "lights" should be – light –.

Col. 6, line 54, after "135°" insert a comma (,).

Col. 15, line 61, before "light" insert – delivered –.

Col. 17, line 5, after "cavity" delete comma (,) and insert period (.).

Col. 17, lines 7-8, after "cavity" delete comma (,) and insert period (.).

Col. 17, line 16, after "elongated" insert a comma (,).

Col. 18, line 12, after "claim" insert – 1 –.

Signed and Sealed this

Second Day of January, 1996

*Attest:*

BRUCE LEHMAN

*Attesting Officer*   *Commissioner of Patents and Trademarks*